United States Patent [19]
Nagahara et al.

[11] Patent Number: 5,426,246
[45] Date of Patent: Jun. 20, 1995

[54] CATALYST FOR DIRECT REDUCTION OF CARBOXYLIC ACID, PROCESS FOR PREPARATION THEREOF AND PROCESS FOR PREPARATION OF ALCOHOL COMPOUND USING THE CATALYST

[75] Inventors: Eiji Nagahara, Osaka; Yasushi Itoi, Daito, both of Japan

[73] Assignee: Arakawa Chemical Industries, Ltd., Osaka, Japan

[21] Appl. No.: 280,460

[22] Filed: Jul. 26, 1994

[30] Foreign Application Priority Data

Jul. 27, 1993 [JP] Japan .................................. 5-205642
Oct. 21, 1993 [JP] Japan .................................. 5-287835

[51] Int. Cl.$^6$ ..................... C07C 29/149; C07C 33/14; C07C 33/30; C07C 31/135
[52] U.S. Cl. .................................. 568/81 T; 502/326; 568/314; 568/396; 568/817; 568/821; 568/831; 568/838; 568/864; 568/885
[58] Field of Search ............... 568/885, 817, 814, 831, 568/864, 838, 821, 396, 314

[56] References Cited

U.S. PATENT DOCUMENTS

| | | | |
|---|---|---|---|
| 4,480,115 | 10/1984 | McGinnis | 568/814 |
| 4,611,085 | 9/1986 | Kitson | 568/885 |
| 4,695,660 | 9/1987 | Otte et al. | 568/831 |
| 4,804,791 | 2/1989 | Kitsom et al. | 568/885 |

FOREIGN PATENT DOCUMENTS

| | | | |
|---|---|---|---|
| 82852 | 3/1992 | Japan | 568/885 |
| 2269116 | 2/1994 | United Kingdom | 568/814 |

*Primary Examiner*—Joseph E. Evans
*Attorney, Agent, or Firm*—Armstrong, Westerman Hattori, McLeland & Naughton

[57] ABSTRACT

Disclosed are a catalyst for directly reducing a carboxylic acid, the catalyst comprising a tin compound and a ruthenium compound supported on a carrier, the catalyst being prepared by the steps of calcining the tin compound in the presence of oxygen after deposition of the tin compound alone on the carrier, and activating the obtained product after deposition of the ruthenium compound on said carrier, a process for preparing the catalyst, and a process for preparing an alcohol compound using the catalyst.

5 Claims, No Drawings

CATALYST FOR DIRECT REDUCTION OF CARBOXYLIC ACID, PROCESS FOR PREPARATION THEREOF AND PROCESS FOR PREPARATION OF ALCOHOL COMPOUND USING THE CATALYST

The present invention relates to a novel catalyst for directly reducing a carboxylic acid, a process for preparing the catalyst and a process for preparing an alcohol compound using the catalyst.

Typical conventional methods for preparing an alcohol compound from a carboxylic acid compound comprise esterifying a carboxylic acid and subjecting the ester to hydrogenolysis in the presence of a catalyst such as copper chromite oxide. However, these methods are disadvantageous for manufacture because an esterification step is essentially executed prior to hydrogenolysis. In view of this problem, there have been proposed various catalysts for direct reduction of a carboxylic acid which enable direct hydrogenolysis of a carboxylic acid compound for conversion to an alcohol compound.

Dirhenium heptoxide, spinel-type copper chromite oxide and the like are known as such catalysts for direct reduction of a carboxylic acid. However, these catalysts are commercially disadvantageous in that a hydrogenolysis reaction using said catalyst requires a high hydrogen pressure of at least 200 atm.

Ruthenium-tin catalysts for directly reducing a carboxylic acid which have been prepared by a sol-gel method are known as having a high activity. When this type of catalyst is used, for example, 9-octadecen-1-ol can be produced by direct hydrogenolysis of oleic acid at a relatively low hydrogen pressure of, e.g., 100 kg/c$^2$ (Japanese Unexamined Patent Publication No. 82852/1992). However, a number of problems are encountered in preparing a catalyst by the sol-gel method. For example, a gel which is difficult to handle is produced in the preparation of the catalyst, and the catalyst is prepared using a tin compound such as tetraethoxytin which is an unstable substance.

Ruthenium-tin catalysts produced by an impregnation method or a co-precipitation method have drawbacks. When this catalyst is used, an alcohol compound is produced at a very low conversion ratio. More problematic is that the catalyst lacks a high activity required for commercial feasibility.

While calcination is effected to secure the active component on a carrier in preparing a catalyst, a ruthenium-containing catalyst entails a further problem of producing a toxic compound during the calcination of ruthenium.

An object of the present invention is to provide a novel catalyst for directly reducing a carboxylic acid, the catalyst being effective, even at a relatively low pressure, for producing an alcohol compound from a carboxylic acid compound in a high yield.

Another object of the invention is to provide a process for preparing said catalyst free of the problems conventionally entailed in the preparation of a catalyst.

A further object of the invention is to provide a process for preparing an alcohol compound from a carboxylic acid compound using said catalyst.

These and other objects of the invention will become more apparent from the following description.

According to the invention, there are provided:

(1) a catalyst for directly reducing a carboxylic acid, the catalyst comprising a tin compound and a ruthenium compound supported on a carrier, the catalyst being prepared by the steps of calcining the tin compound in the presence of oxygen after deposition of the tin compound alone on the carrier, and activating the obtained product after deposition of the ruthenium compound on said carrier, (2) a process for preparing a catalyst for directly reducing a carboxylic acid, the process comprising the steps of calcining a tin compound in the presence of oxygen after deposition of the tin compound alone on a carrier, and activating the obtained product after deposition of a ruthenium compound on said carrier, and (3) a process for preparing an alcohol compound from a carboxylic acid compound, the process comprising subjecting the carboxylic acid compound to hydrogenolysis in the presence of said catalyst.

The inventor of this invention conducted extensive research in view of said prior art problems and found that the objects of the invention can be achieved by the ruthenium-tin catalyst prepared by the above specific process, The present invention has been completed on the basis of this novel finding.

In the preparation of the catalyst for directly reducing a carboxylic acid according to the invention, it is essential, first, to calcine the tin compound in the presence of oxygen after deposition of the tin compound alone on a carrier.

Carriers to be used in the present invention include those heretofore known such as alumina, titania, silica, zirconia, etc. among which alumina is preferred. The shape of useful carriers is not specifically limited and useful carriers may be in the shape of molded products, e.g. granules, globes, extrusions, pellets, honeycomb-shaped moldings, etc. or non-molded products such as powders.

As to tin compounds, it is preferred to use at least one member selected from the group consisting of bis(tributyltin) oxide, potassium stannate, sodium stannate, tin octylate and tributyltin chloride which are effectively used to give a catalyst of high activity. The methods of placing the tin compound on a carrier are not specifically limited, and various conventional techniques can be employed, for example, an impregnation method, co-precipitation method, ion exchange method, etc.

After deposition of the tin compound on the carrier, calcination is conducted in the presence of oxygen. When calcination is not performed at this stage in the preparation of a catalyst, a catalyst of high activity can not be produced and, accordingly, the objects of the present invention can not be accomplished. On the other hand, if calcination is done not only after deposition of the tin compound on the carrier but also after deposition of the ruthenium compound thereon, there is posed a further problem of producing a toxic compound as well as the problem of failing to produce a catalyst of high activity.

The calcination is effected in the present invention at a temperature of 400° C. or higher. At lower than 400° C., the calcination produces little or no effect, failing to provide a catalyst of high activity. The upper limit of the calcination temperature is not specifically limited, but is usually up to 1,200° C. above which the sintering of metallic oxide and the structural degradation of carrier may occur. A preferred calcination temperature is in the range of about 500° to about 900° C. The calcination time is in the range of about 0.5 to about 10 hours. The calcination methods are not critical in the present invention, and include methods using a muffle furnace, flow-type methods, etc. The term "in the presence of oxygen" is used herein to mean "in a gas stream or an atmosphere containing oxygen, for example, air, artificial oxygen, pure oxygen, a gas mixture containing oxygen or the like, etc."

In the preparation of the catalyst of the invention, it is further essential to activate the product after deposition of the ruthenium compound on the carrier following the calcination of the tin compound supported on said carrier.

Examples of useful ruthenium compounds are ruthenium salts such as ruthenium nitrosyl nitrate complex, ruthenium nitrate, ruthenium chloride, etc., organic ruthenium such as acetylacetone ruthenium, ruthenium chelate complexes, e.g. ruthenium combined with a chelating agent such as ethylenediamine, phenanthroline, bipyridyl or the like, carbonyl ruthenium, etc., ruthenium alkoxide, and so on. The methods of placing the ruthenium compound on the carrier are not critical and include various conventional techniques, for example, an impregnation method, co-precipitation method, ion exchange method, etc., namely the same methods employable for the deposition of the tin compound.

In the present invention, activation is essentially conducted after deposition of the ruthenium compound on the carrier. The methods of activation are not critical in the present invention. Preferred activation methods are, for example, reduction methods such as a gas phase reduction method, liquid phase reduction method, etc.

Gas phase reduction methods which are employable include hydrogen gas-flow reduction methods, and reduction methods in which a reducing agent such as hydrazine is passed through a stream of water vapor for reduction. Stated more specifically, the hydrogen gas-flow method comprises reducing the compound in a stream of hydrogen at a temperature of 400° C. or higher. At lower than 400° C., only a low reducing power is attained, consequently making it difficult to produce a catalyst of high activity. The reduction temperature is not specifically limited insofar as a high reducing power is provided. Yet, if consideration is given to prevention of energy loss and sintering of metal, the reduction is conducted preferably at a temperature of about 400° to about 1,000° C. The reduction time is at least 0.1 hour, preferably 0.5 to 20 hours.

Liquid phase reduction methods to be used include a formalin reduction method, hydrazine reduction method, lithium aluminum hydride reduction method, etc. These methods can provide a reducing power as high as or higher than gas phase reduction methods.

The thus obtained catalyst of the invention contains, calculated as the metals and based on the weight of the catalyst, about 0.01 to about 20% by weight, preferably about 0.1 to about 10% by weight, of the ruthenium compound supported on the carrier, and about 0.1 to about 50% by weight of the tin compound supported thereon. The molar ratio, calculated as the metals, of the ruthenium compound to the tin compound supported on the carrier is 1:0.1 to 1:20, preferably 1:1 to 1:10. The ratio outside said range is undesirable because the catalyst is not imparted a high activity sufficient to directly reduce a carboxylic acid.

It is difficult to specify the distribution and activation degree of the metal having a hydrogenation activity on the surface of the obtained catalyst. These characteristics, if assessed in terms of a gas chemisorption amount, are expressed as a gas adsorption of, per gram of the catalyst, 0 to about 0.5 ml of hydrogen, 0 to about 4 ml of carbon monoxide and about 1 to about 11 ml of oxygen.

Using the catalyst of this invention for directly reducing a carboxylic acid, the corresponding alcohol compound can be produced from a carboxylic acid compound by hydrogenolysis of carboxyl groups in the carboxylic acid compound, that is, by a single step, further advantageously in a high yield.

Various conventional carboxylic acid compounds having at least one carboxyl group in the molecule can be used for conversion to alcohol compounds using the catalyst of the invention. The catalyst of the invention has the advantage of being effectively used for carboxylic acid compounds having branched-chain saturated or unsaturated carboxyl groups which have been heretofore considered difficult to reduce, and also for carboxylic acid compounds with an aromatic ring in which the carboxyl group has been considered prone to decompose. Specific examples of such carboxylic acid compounds are alicyclic carboxylic acids such as rosin, cyclohexanecarboxylic acid, naphthenic acid, cyclopentanecarboxylic acid, cycloheptanecarboxylic acid, methylcyclohexanecarboxylic acid, etc.; linear or branched-chain saturated or unsaturated aliphatic carboxylic acids such as formic acid, acetic acid, butyric acid, valeric acid, pivalic acid, 1-hexanoic acid, 2-ethylhexanoic acid, lauric acid, oleic acid, linolic acid, linolenic acid, elaidic acid, stearic acid, arachic acid, myristic acid, palmitic acid, eicosenoic acid, etc.; carboxylic acids having conjugated groups such as acetoacetic acid, acrylic acid, etc.; aromatic carboxylic acids such as benzoic acid, phenylacetic acid, benzylic acid, benzoylbenzoic acid, etc.; hydroxycarboxylic acids such as mandelic acid, lactic acid, hydroxybutylic acid, etc.; and amino acids.

A batchwise method or a flow method (fixed bed or fluidized bed method) can be employed for a hydrogenolysis reaction.

The hydrogen pressure in the hydrogenolysis is about 10 to about 300 kg/cm$^2$, preferably about 50 to about 200 kg/cm$^2$ in the batchwise method, and is about 1 to about 300 kg/cm$^2$, preferably about 1 to about 200 kg/cm$^2$ in the flow method. The hydrogenolysis reaction, whether by the batchwise method or by the flow method, can proceed as desired even at a relatively low pressure. According to the invention, the flow method, particularly a fixed bed flow method, has the advantage of producing an alcohol compound even if carried out at atmospheric pressure. Hydrogenolysis is feasible in the present invention even if the hydrogen pressure is lower than about 10 kg/cm$^2$ in the batchwise method, and lower than 1 kg/cm$^2$ in the flow method. The reaction temperature is in the range of about 150° to about 400° C., preferably about 200° to about 300° C., in any of said reaction methods.

The hydrogen and the carboxylic acid compound are supplied in the flow method at a volume ratio of hydrogen (amount supplied per unit time):carboxylic acid compound (amount supplied per unit time) of about 1:1 to about 5,000:1, preferably 500:1 to 3,000:1. A supply of hydrogen in less than said volume ratio reduces the reactivity, whereas a supply of hydrogen in more than said volume ratio means excess supply and an increased cost. Hence its supply outside said ratio is undesirable. The liquid hourly space velocity (LHSV) of the materials is in the range of about 0.01 to about 25, preferably about 0.1 to about 2. The LHSV outside said range is undesirable because a LHSV of less than 0.01 leads to a prolonged reaction time and thus to a higher cost, whereas a LHSV of more than 25 decreases the reactivity.

In the batchwise method, the catalyst is used in an amount of about 0.1 to about 50 parts by weight, preferably about 1 to about 20 parts by weight, per part by weight of the carboxylic acid compound, and the reaction time is about 1 to about 100 hours, preferably about 1 to about 50 hours.

While a solvent need not be used in the hydrogenolysis, it is possible, when required, to use a solvent such as toluene, decalin, dioxane, diglyme, n-heptane, water, acetone, benzene, pyridine, diethyl ether, tetrahydrofuran, cyclohexane, methylcyclohexane, etc.

The present invention provides a catalyst for directly reducing a carboxylic acid which enables the preparation of an alcohol compound directly from a carboxylic acid compound, and a process for preparing the catalyst. Using the catalyst of the invention, an alcohol compound can be produced from a carboxylic acid compound in a high yield even at a relatively low pressure. As described hereinbefore, the catalyst of the invention entails no problem in the preparation thereof.

The present invention will be described below in more detail with reference to the following Examples and Comparative Example to which, however, the present invention is not limited. The percentages in the Examples are all by weight unless otherwise specified.

EXAMPLE 1

(1) Preparation of catalyst

To 15.0 g of alumina was added 25 g of a 20% aqueous solution of potassium stannate. The mixture was stirred for 15 hours to place the potassium stannate on the alumina, and the water was distilled off. The residue was calcined in a stream of air at 800° C. for 5 hours and left to cool. Then 18.0 g of a 5% aqueous solution of ruthenium nitrosyl nitrate complex was added to the calcined product. The mixture was stirred for 15 hours to place the complex on the calcined product, and the solvent was distilled off. The residue was reduced in a stream of hydrogen at 450° C. for 4 hours, giving a catalyst. The obtained catalyst contained, calculated as the metals, 5% of Ru and 11.7% of Sn based on the weight of the catalyst. The gas adsorption amounts of the catalyst were 0.05 ml/g of $H_2$, 0.10 ml/g of CO and 8.39 ml/g of $O_2$.

(2) Hydrogenolysis

Into a 500 ml-vol. autoclave equipped with an electromagnetic stirrer were placed 50.0 g of a rosin (acid value 166) and 95 g of diglyme. A 5.0 g portion of the catalyst obtained above in (1) was added. The mixture was subjected to a hydrogenolysis reaction at a hydrogen pressure of 100 kg/cm² and 260° C. After a 4 hour-reaction, the reaction mixture was filtered to separate the catalyst. The solvent was distilled off by an evaporator, giving a rosin alcohol having a hydroxyl value of 175. The yield of the rosin alcohol was evaluated as 100 mole % from the theoretical hydroxyl value (175) calculated from the acid value of the starting material. The obtained product was subjected to gel permeation chromatography (hereinafter called "GPC") and high performance liquid chromatography (hereinafter called "HPLC") for analysis, whereby it was confirmed that the rosin alcohol alone was produced without the formation of a by-product.

EXAMPLE 2

A catalyst was produced by conducting the same procedure as in (1) of Example 1 with the exception of using 30 g of a 35% solution of bis(tributyltin) oxide in n-heptane as a tin compound. The catalyst contained, calculated as the metals, 5% of Ru and 23.4% of Sn, based on the weight of the catalyst. The gas adsorption amounts of the catalyst were zero of $H_2$, zero of CO and 9.23 ml/g of $O_2$.

Hydrogenolysis was carried out in the same manner as in (2) of Example 1 with the exception of using the catalyst obtained above, giving a rosin alcohol having a hydroxyl value of 174. The yield of the rosin alcohol was evaluated as 99 mole % from the theoretical hydroxyl value (175) calculated from the acid value of the starting material. The obtained product was subjected to GPC and HPLC for analysis, whereby it was confirmed that the rosin alcohol alone was produced without the formation of a by-product.

EXAMPLE 3

A catalyst was produced by conducting the same procedure as in (1) of Example 1 with the exception of using 30 g of a 15% aqueous solution of sodium stannate as a tin compound. The catalyst contained, calculated as the metals, 5% of Ru and 11.7% of Sn, based on the weight of the catalyst. The gas adsorption amounts of the catalyst were 0.03 ml/g of $H_2$, 0.09 ml/g of co and 8.07 ml/g of $O_2$.

Hydrogenolysis was performed in the same manner as in (2) of Example 1 with the exception of using the catalyst obtained above, giving a rosin alcohol having a hydroxyl value of 168. The yield of the rosin alcohol was evaluated as 96 mole % from the theoretical hydroxyl value (175) calculated from the acid value of the starting material. The obtained product was subjected to GPC and HPLC for analysis, whereby it was confirmed that the rosin alcohol alone was produced without the formation of a by-product.

EXAMPLE 4

A catalyst was produced by following the same procedure as in (1) of Example 1 with the exception of using 40 g of a 35% solution of tributyltin chloride in n-heptane as a tin compound. The catalyst contained, calculated as the metals, 5% of Ru and 23.4% of Sn, based on the weight of the catalyst. The gas adsorption amounts of the catalyst were zero of $H_2$, zero of CO and 9.13 ml/g of $O_2$.

Hydrogenolysis was effected in the same manner as in (2) of Example 1 with the exception of using the catalyst obtained above, giving a rosin alcohol having a hydroxyl value of 163. The yield of the rosin alcohol was evaluated as 93 mole % from the theoretical hydroxyl value (175) calculated from the acid value of the starting material. The obtained product was subjected to GPC and HPLC for analysis, whereby it was confirmed that the rosin alcohol alone was produced without the formation of a by-product.

EXAMPLE 5

Hydrogenolysis was carried out in the same manner as in (2) of Example 1 with the exception of using lauric acid in place of the rosin, giving a lauryl alcohol. The obtained product was subjected to gas chromatography (hereinafter called "GC") and GPC for analysis. It was confirmed that the lauryl alcohol was produced in a yield of 94 mole %.

EXAMPLE 6

Hydrogenolysis was conducted in the same manner as in (2) of Example 1 with the exception of using benzoic acid in place of the rosin, giving a benzyl alcohol. The obtained product was analyzed by GC and GPC, whereby it was confirmed that the benzyl alcohol was produced in a yield of 94 mole %.

EXAMPLE 7

Hydrogenolysis was performed in the same manner as in (2) of Example 1 with the exception of using 1-hexanoic acid in place of the rosin, giving 1-hexanol. The obtained product was analyzed by GC and GPC, whereby it was confirmed that the 1-hexanol was produced in a yield of 86 mole %.

EXAMPLE 8

Hydrogenolysis was conducted in the same manner as in (2) of Example 1 with the exception of using cyclohexanecarboxylic acid in place of the rosin, giving cyclohexanemethanol. The obtained product was analyzed by GC and GPC, whereby it was confirmed that the cyclohexanemethanol was produced in a yield of 74 mole %.

EXAMPLE 9

Hydrogenolysis was performed in the same manner as in (2) of Example 1 with the exception of using 2-ethylhexanoic acid in place of the rosin, giving 2-ethylhexanol. The obtained product was analyzed by GC and GPC, whereby it was confirmed that the 2-ethylhexanol was produced in a yield of 67 mole %.

EXAMPLE 10

A 20% solution of a rosin in diethylene glycol dibutyl ether was passed through a reactor of the fixed bed type which was filled with 60 g of the catalyst prepared in (1) of Example 1 to conduct hydrogenolysis under reaction conditions of a temperature of 260° C., a pressure of 25 kg/cm$^2$, a volume ratio of hydrogen (amount supplied per unit time) to rosin (amount supplied per unit time and contained in the solution) of 2,400:1 and a liquid hourly space velocity (LHSV) of the rosin solution of 0.3. The obtained reaction mixture was purified by distillation in a vacuum, giving a rosin alcohol of 186 in hydroxyl value. The yield of the obtained product was evaluated as 100 mole % from the theoretical hydroxyl value (186) of rosin alcohol. The obtained product was analyzed by GPC and HPLC, whereby it was confirmed that the rosin alcohol alone was produced without the formation of a by-product.

EXAMPLE 11

Hydrogenolysis was performed in the same manner as in Example 10 with the exception of changing the reaction temperature to 280° C. and the volume ratio of hydrogen (amount supplied per unit time) to rosin (amount supplied per unit time and contained in the solution) to 1,200:1, giving a rosin alcohol of 186 in hydroxyl value. The yield of the obtained product was evaluated as 100 mole % from the theoretical hydroxyl value (186) of rosin alcohol. The obtained product was analyzed by GPC and HPLC, whereby it was confirmed that the rosin alcohol alone was produced without the formation of a by-product.

EXAMPLE 12

Hydrogenolysis was carried out in the same manner as in Example 10 with the exception of changing the reaction pressure to 10 kg/cm$^2$, giving a rosin alcohol of 186 in hydroxyl value. The yield of the rosin alcohol was evaluated as 100 mole % from the theoretical hydroxyl value (186) of rosin alcohol. The obtained product was analyzed by GPC and HPLC, whereby it was confirmed that the rosin alcohol alone was produced without the formation of a by-product.

EXAMPLE 13

Hydrogenolysis was conducted in the same manner as in Example 10 with the exception of changing the LHSV to 0.5, giving a rosin alcohol of 186 in hydroxyl value. The yield of the rosin alcohol was evaluated as 100 mole % from the theoretical hydroxyl value (186) of rosin alcohol. The obtained product was analyzed by GPC and HPLC, whereby it was confirmed that the rosin alcohol alone was produced without the formation of a by-product.

COMPARATIVE EXAMPLE 1

To 15.0 g of alumina was added 40 g of a 15% solution of tin (II) chloride in isopropyl alcohol. The mixture was stirred for 15 hours, and the solvent was distilled off. The residue was calcined in a flowing air at 800° C. for 5 hours and left to cool. A 18.0 g quantity of a 5% solution of ruthenium nitrosyl nitrate complex was added. Then the mixture was stirred for 15 hours to place the tin (II) chloride on the alumina, and the solvent was distilled off. The residue was reduced in a stream of hydrogen at 450° C. for 4 hours, giving a catalyst. Hydrogenolysis was carried out in the same manner as in (2) of Example 1 with the exception of using the catalyst thus obtained, producing a rosin alcohol of 94 in hydroxyl value. The yield of the rosin alcohol was evaluated as 54 mole % from the theoretical hydroxyl value of rosin alcohol calculated from the acid value of the starting material.

We claim:

1. A process for preparing an alcohol compound from a carboxylic acid compound, the process comprising subjecting the carboxylic acid compound to hydrogenolysis in the presence of a catalyst which comprises a tin compound and a ruthenium compound supported on a carrier, said catalyst being prepared by the steps of calcining the tin compound in the presence of oxygen after deposition of the tin compound alone on the carrier, and activating the obtained product after deposition of the ruthenium compound on said carrier.

2. A process according to claim 1, wherein the ruthenium compound and the tin compound are supported on the carrier in the proportions of, calculated as the metals, about 0.01 to about 20% by weight of the ruthenium compound and about 0.1 to about 50% by weight of the tin compound, based on the weight of the catalyst.

3. A process according to claim 1, wherein the tin compound is at least one member selected from the group consisting of bis(tributyltin) oxide, potassium stannate, sodium stannate, tin octylate and tributyltin chloride.

4. A process according to claim 1, wherein the calcination is conducted at a temperature of 400° C. or higher.

5. A process according to claim 1, wherein the activation is conducted by reduction in a stream of hydrogen at a temperature of 400° C. or higher.

* * * * *